United States Patent
Keller et al.

(10) Patent No.: US 11,628,407 B2
(45) Date of Patent: Apr. 18, 2023

(54) HOLLOW FIBER MEMBRANE HAVING IMPROVED DIFFUSION PROPERTIES

(71) Applicant: FRESENIUS MEDICAL CARE DEUTSCHLAND GMBH, Bad Homburg (DE)

(72) Inventors: Torsten Keller, St. Wendel (DE); Roland Sander, St. Wendel (DE); Igor Raiko; Christian Finkler, Nonnweiler (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 292 days.

(21) Appl. No.: 16/493,311

(22) PCT Filed: Mar. 16, 2018

(86) PCT No.: PCT/EP2018/056689
§ 371 (c)(1),
(2) Date: Sep. 12, 2019

(87) PCT Pub. No.: WO2018/167280
PCT Pub. Date: Sep. 20, 2018

(65) Prior Publication Data
US 2020/0030751 A1    Jan. 30, 2020

(30) Foreign Application Priority Data
Mar. 17, 2017    (DE) .................... 10 2017 204 524.8

(51) Int. Cl.
*B01D 69/08* (2006.01)
*A61M 1/16* (2006.01)
(Continued)

(52) U.S. Cl.
CPC .............. *B01D 69/084* (2013.01); *A61L 2/07* (2013.01); *A61M 1/1621* (2014.02);
(Continued)

(58) Field of Classification Search
None
See application file for complete search history.

(56) References Cited

U.S. PATENT DOCUMENTS 4,840,769 A * 6/1989 Nejigaki ............. A61M 1/1686
                                                  210/636
5,591,344 A * 1/1997 Kenley ............... A61M 1/3647
                                                  210/764
(Continued)

FOREIGN PATENT DOCUMENTS

CN      204731152 U    10/2015
DE        10007327 A1   8/2001
(Continued)

OTHER PUBLICATIONS

"Ultrafiltration Membranes and Applications", edited by Anthony Cooper, Polymer Science and Technology, vol. 13, published 1980. (Year: 1980).*
(Continued)

*Primary Examiner* — Jonathan M Peo
(74) *Attorney, Agent, or Firm* — Kilyk & Bowersox, P.L.L.C.

(57) ABSTRACT

The invention relates to an undulated thermostable hollow fiber membrane of reduced wall thickness, wherein the wall thickness amounts to 20 μm or greater and 30 μm or less and the waveform of the hollow fiber membrane exhibits a wavelength in the range of from more than 1 mm and less than 5 mm. In particular, the invention relates to a method for producing an undulated thermostable hollow fiber membrane of lower wall thickness.

15 Claims, 1 Drawing Sheet

Figure 1:
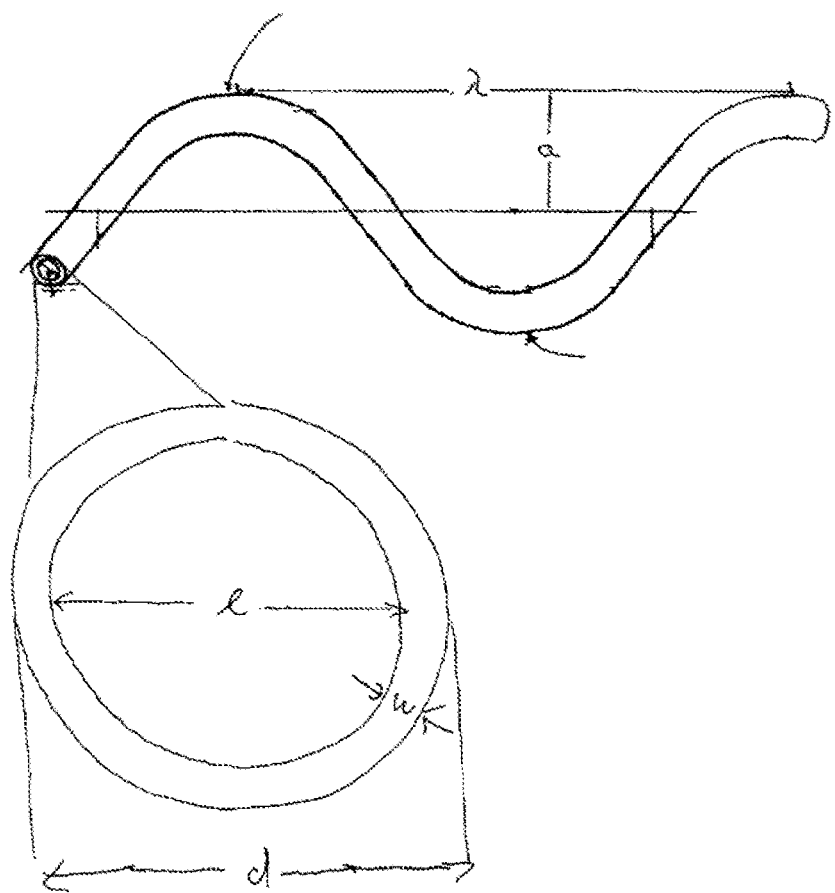

(51) Int. Cl.
*A61L 2/07* (2006.01)
*B01D 61/24* (2006.01)
*B01D 63/02* (2006.01)
*B01D 71/68* (2006.01)

(52) U.S. Cl.
CPC ......... *A61M 1/1686* (2013.01); *B01D 61/243* (2013.01); *B01D 63/02* (2013.01); *B01D 69/081* (2013.01); *B01D 69/087* (2013.01); *B01D 71/68* (2013.01); *A61L 2202/24* (2013.01); *A61M 2207/00* (2013.01)

(56) References Cited

U.S. PATENT DOCUMENTS

| | | | |
|---|---|---|---|
| 5,851,394 | A | 12/1998 | Shibata et al. |
| 2003/0155294 | A1* | 8/2003 | Heilmann ............ B01D 61/28 210/321.78 |
| 2009/0078641 | A1* | 3/2009 | Monden ............... B01D 69/087 210/321.6 |
| 2009/0261038 | A1 | 10/2009 | Heim |
| 2010/0294714 | A1* | 11/2010 | Buck .................... B01D 69/087 210/500.23 |
| 2012/0175299 | A1 | 7/2012 | Maurer |
| 2013/0020237 | A1* | 1/2013 | Wilt .................... A61M 1/3627 210/85 |
| 2013/0338297 | A1* | 12/2013 | Ford ...................... B01D 71/44 524/502 |
| 2015/0054197 | A1* | 2/2015 | Vecitis ............... B01D 67/0013 264/299 |
| 2015/0314057 | A1 | 11/2015 | Labib et al. |
| 2015/0343394 | A1* | 12/2015 | Hayashi ............... B01D 67/002 264/209.2 |
| 2016/0207009 | A1* | 7/2016 | Menda .................. B01D 69/06 |
| 2019/0381462 | A1 | 12/2019 | Keller et al. |

FOREIGN PATENT DOCUMENTS

| | | | |
|---|---|---|---|
| DE | 102011008222 | A1 | 7/2012 |
| EP | 0305787 | A1 | 3/1989 |
| EP | 2253371 | A1 | 11/2010 |
| EP | 2659914 | A1 | 11/2013 |
| JP | S5722762 | A | 2/1982 |
| JP | S57194007 | A | 11/1982 |
| JP | 61200805 | A | 9/1986 |
| JP | 61200806 | A | 9/1986 |
| JP | S61242604 | A | 10/1986 |
| JP | 921024 | A | 1/1997 |
| JP | 2002143654 | A | 5/2002 |
| JP | 2003010654 | A | 1/2003 |
| JP | 2006051094 | A | 2/2006 |
| JP | 2008155009 | A | 7/2008 |
| JP | 2010036127 | A | 2/2010 |
| JP | 2010233980 | A | 10/2010 |
| JP | 2010233991 | A | 10/2010 |
| JP | 5601752 | B2 | 10/2014 |

OTHER PUBLICATIONS

International Search Report and Written Opinion issued in corresponding International Patent Application No. PCT/EP2018/056689 (with English translation of International Search Report) dated Jul. 9, 2018 (10 pages).
International Preliminary Report on Patentability issued in corresponding International Patent Application No. PCT/EP2018/056689 dated Sep. 17, 2019 (with English translation) (12 pages).
Office Action issued in corresponding Chinese Patent Application No. 201880018335.2 dated Jun. 26, 2021 (English translation only)(13 pages).
Deng "Blood Purification Nursing Handbook," Shandong University Press, Sep. 2008, pp. 33-34 (4 pages).
"Blood Purification Apparatus," Jan. 1, 2016 (with partial English translation)(5 pages).
"Biocompatibility of Dialytic," Mar. 25, 2010 (with partial English translation)(5 pages).
"Up-to-Date High Performance Dialyzer," Mar. 15, 2016 (with partial English translation)(12 pages).
"The New High Performance Dialyzer," Jul. 10, 2000 (with partial English translation)(9 pages).
Third Party Observation issued in corresponding European Patent Application No. 18720105.8 dated Jul. 27, 2021 (15 pages).
Wei Xia "Design and Production of Industrial Textiles," Donghua University Press, Aug. 2009 (3 pages) (relevance set forth in English translation of Chinese Office Action submitted herewith).
Chen Guanwen, et al., "New Progress and Engineering application of Membrane Technoogy," National Defense Industry Press, Aug. 2013 (5 pages) (relevance set forth in English translation of Chinese Office Action submitted herewith).
"Chemical Encyclopedia," editorial board of "Chemical Encyclopedia" Chemical Industry Press, Sep. 1998 (3 pages) (relevance set forth in English translation of Chinese Office Action submitted herewith).
Office Action issued in corresponding Chinese Patent Application 201880018335.2 dated Jun. 7, 2022 (with English translation) (25 pages).
Office Action issued in corresponding Korean Patent Application 10-2019-7030489 dated Oct. 5, 2022 (6 pages).

* cited by examiner

HOLLOW FIBER MEMBRANE HAVING IMPROVED DIFFUSION PROPERTIES

This application is a National Stage Application of PCT/EP2018/056689, filed Mar. 16, 2018, (published as WO 2018/167280) which claims priority to German Patent Application No. 10 2017 204 524.8, filed Mar. 17, 2017 (published as DE 10 2017 204 524 A1).

FIELD OF THE INVENTION

The invention relates to an undulated hollow fiber membrane of reduced wall thickness. The invention further relates to a method for producing an undulated hollow fiber membrane of lesser wall thickness. Furthermore, the invention relates to a hollow fiber membrane dialyzer having a plurality of hollow fiber membranes of lesser wall thickness. The invention also further relates to the production of a hollow fiber membrane and a hollow fiber membrane dialyzer having a plurality of undulated hollow fiber membranes of lesser wall thickness.

BACKGROUND OF THE INVENTION

Hollow fiber membranes are extensively used in the filtration of fluids. In medical technology, hollow fiber membranes are in particular used in different forms of extracorporeal blood treatment. In extracorporeal blood treatment, particularly hemodialysis, a hollow fiber membrane dialyzer removes toxic uremic blood components. Generally speaking, blood taken from a patient is thereby conveyed through the cavity of the hollow fiber membranes of the hollow fiber membrane dialyzer while, depending on the form of treatment or type of extracorporeal blood treatment, an aqueous fluid led along the exterior of the hollow fiber membrane collects the separated blood components and transports them out of the hollow fiber membrane dialyzer. A hollow fiber membrane dialyzer thus comprises a total of two inlets and two outlets. The interior and exterior of the hollow fiber membranes are also called the blood side and the dialysate side according to this principle of extracorporeal blood treatment. The walls of the hollow fiber membranes are thereby designed as porous membranes so that blood component substances can be transported from the blood side to the dialysate side of the hollow fiber membrane through the membrane wall of the hollow fiber membrane. The prevailing transport mechanism of low-molecular uremic toxins such as for example urea is predominantly dictated by diffusive processes while toxins of medium-range molecular weight up to 50 kDa are separated via convective processes, for which a so-called transmembrane pressure difference needs to be generated during dialyzer operation.

The separation efficiency with which toxic blood components can be separated from the blood is called clearance. Determining the clearance is defined for example in the DIN/EN/ISO 8637:2014 standard and is to be ascertained for hollow fiber membrane dialyzers based on the methods described therein. Accordingly, in addition to the parameters of the testing procedure, the measured clearance is in particular influenced by the properties of the hollow fiber membranes and the hollow fiber membrane dialyzers manufactured therefrom. Playing a particularly important role is thereby the nature of the pores and the geometry of the hollow fiber membrane as well as the geometry of the hollow fiber membrane dialyzer. Determining the characteristic separation efficiency of a hollow fiber membrane can only occur on a hollow fiber membrane filter of geometrically defined construction. The flow conditions of the test fluids must also be specified when characterizing the membrane. Urea is frequently used as the characteristic uremic toxin of lowest molecular weight for standard-based clearance measurements. It has, however, been shown that similar clearance values are determined for urea as for sodium ions. Clearance determination using sodium ions is a simpler and more reliable process.

In order to improve extracorporeal blood treatments, improving the clearance is an ongoing goal in hemodialyzer development. Proposed in the prior art in this regard is for example configuring hollow fiber membranes in waveform. The waveform is thereby contingent on two parameters, wavelength and amplitude. The waveform is typically disposed on the hollow fiber membranes mechanically by suitable undulating tools. The waveform thereby creates a spacing between the close packed hollow fiber membranes in a hollow fiber membrane dialyzer. Doing so thereby prevents the hollow fiber membranes from abutting against each other, which enables improved flow for the dialysate relative same in the hollow fiber membrane dialyzer. This increases the transmembrane substance transfer and thus also the clearance of the blood components to be separated.

Reducing the wall thickness to improve the hollow fiber membrane clearance is further known. Reducing the wall thickness thereby effects a shortening of the diffusion path which a low molecular blood component to be separated needs to travel in order to pass through the membrane wall and thereby correlates to a decrease in the diffusion resistance. Cellulose-based/cellulose derivative-based hollow fiber membranes for extracorporeal blood treatment having a wall thickness of less than 15 µm which are of very compact design and characterized by a high density are known in the prior art. At present, porous hollow fiber membranes based on polymers such as polysulfone and generally of a wall thickness of 35 to 45 µm dominate the medical technology market.

It has, however, been shown that the typical prior art waveforms of 5 mm or more along with a reduced hollow fiber membrane wall thickness does not in fact lead to an increase in clearance but rather to a worsening. This was in particular observed with heat-sterilized hollow fiber membrane dialyzers. The reason for this is attributed to the heat sterilization of a hollow fiber membrane dialyzer and the associated material expansions and relaxations at higher temperatures. In heat sterilization, hollow fiber membrane dialyzers are usually heated to temperatures greater than 100° C. The thermal effect of the heat sterilization process obviously leads to more pronounced relaxing of the waveform in hollow fiber membranes of reduced wall thickness than is the case with hollow fiber membranes of greater wall thickness albeit the same wavelength and amplitude. As a result, the flowability relative the hollow fiber membranes on the dialysate side of a hollow fiber membrane dialyzer worsens to such a great extent that despite the reduced diffusion resistance of the lesser membrane wall thickness, a decrease in clearance compared to an alternative hollow fiber membrane dialyzer of greater wall thickness can be observed. This clearance decrease effect occurs particularly when water vapor is used as the heat-sterilizing medium. The thermal action and the water exposure intensifies the relaxation effect.

Accordingly, undulated hollow fiber membranes of lesser wall thicknesses prove thermally unstable compared to those of greater wall thicknesses. Hence, previous attempts at constructing heat-sterilizable hollow fiber membrane dialyzers exhibiting improved clearance as a result of using undulated hollow fiber membranes of reduced wall thickness have also been unsuccessful.

Hollow fiber membranes of waveforms are described in the prior art. EP 1 685 862 A1 describes a polysulfone-based and polyvinlypyrrolidone-based hollow fiber membrane having a wall thickness of 45 μm, a wavelength range of from 2 to 20 mm, and an amplitude from 0.1 to 5 mm. However, preferential wavelengths are from 4 mm to 8 mm and preferential amplitudes are 0.2 to 1 mm. Hollow fiber membranes of such wall thicknesses and low 2 mm wavelength range are to be classified as thermally unstable.

EP 1 671 695 A1 describes a hollow fiber membrane dialyzer having undulating hollow fiber membranes, the wavelength of which derives from parameters of the hollow fiber membrane geometry and the housing geometry. A calculative wavelength of 1.4 to 13.1 mm is indicated, whereby wavelengths relevant to practical applications are indicated at 4 to 12 mm. At the given hollow fiber membrane and filter housing geometric parameters, the waveform of the hollow fiber membranes fills the filter housing space in specific manner, thereby enabling fluid to advantageously fill the hollow fiber membrane dialyzer prior to the first use.

EP 2 253 371 A1 describes an undulating hollow fiber membrane having a wall thickness of 25 to 45 μm, preferentially 35 μm, which can exhibit a wavelength of 5 to 10 mm and an amplitude between 0.1 and 0.5 mm.

Task of the Invention

Previously known techniques of increasing the clearance of heat-sterilizable hollow fiber membranes by undulated hollow fiber membrane design are not applicable to hollow fiber membranes of lower wall thickness. One objective of the present invention was therefore to provide an undulated hollow fiber membrane of low wall thickness which exhibits sufficient thermal stability and thus largely retains its efficiency properties even after heat sterilization.

A further associated objective of the invention was that of providing a method for producing such a thermostable hollow fiber membrane.

A further objective of the invention consisted of providing a heat-sterilized hollow fiber membrane dialyzer comprising hollow fiber membranes of low wall thickness which exhibits high filtration efficiency properties.

A further associated objective of the invention was that of providing a method for producing such hollow fiber membrane dialyzers comprising undulated hollow fiber membranes of low wall thickness.

SUMMARY OF THE INVENTION

In a first aspect, the invention relates to an undulated hollow fiber membrane, comprising a first hydrophobic polymer, having a wall thickness of 20 μm or greater and 30 μm or less, wherein the waveform exhibits a wavelength of greater than 1 mm and less than 5 mm, in particular less than 4 mm.

In one embodiment according to the first aspect of the invention, the undulated hollow fiber membrane is characterized by the waveform having an amplitude of from 0.005 to 0.15 mm, in particular from 0.01 to 0.12 mm.

In a further embodiment according to the first aspect of the invention, the undulated hollow fiber membrane is characterized by the luminal diameter of the hollow fiber membrane amounting to 160 to 230 μm.

In a further embodiment according to the first aspect of the invention, the undulated hollow fiber membrane is characterized by the waveform being substantially sinusoidal.

In a further embodiment according to the first aspect of the invention, the undulated hollow fiber membrane is characterized by at least one first hydrophobic polymer being selected from the polyarylether (polysulfone, polyarylketone, polyetherketone), polyamide, polyester, polycarbonate, polyacrylate and methacrylate, polymethacrylimide, polyvinylidenfluoride, polyimide or polyacrylnitrile group or the copolymers comprising corresponding monomer units of the cited polymers or the compounds of the cited polymers.

In a further embodiment according to the first aspect of the invention, the undulated hollow fiber membrane is characterized by the hollow fiber membrane comprising at least one second hydrophilic polymer and by the at least one second polymer being selected from the polyvinylpyrrolidone or polyethylene glycol group or compounds thereof.

In a further embodiment according to the first aspect of the invention, the undulated hollow fiber membrane is characterized by the porosity of the hollow fiber membrane being greater than 65%, in particular greater than 70%, further particularly greater than 72%.

Typically, the wave of the inventive hollow fiber membrane is a longitudinal wave as is also depicted in the FIG. 1 embodiment.

In a second aspect, the invention relates to a method for producing an undulated hollow fiber membrane containing at least one first hydrophobic polymer, comprising the steps:
Producing a hollow fiber membrane having a wall thickness of 20 μm or greater and 30 μm or less from a spinning material in a spinning and phase inversion process,
Providing at least one undulating tool, orientating the undulating tool if need be, in order to produce a waveform of predetermined wavelength and amplitude,
Processing the hollow fiber membrane with the undulating tool so as to yield an undulation wavelength of more than 1 mm and less than 5 mm, in particular less than 4 mm.

In a further embodiment according to the second aspect of the invention, the method for producing an undulated hollow fiber membrane is characterized by the undulating tool comprising two intermeshing gears, between which the hollow fiber membrane is passed.

In a further embodiment according to the second aspect of the invention, the method for producing an undulated hollow fiber membrane is characterized by the gearwheels of the undulating tool exhibiting a tooth head spacing of more than 1 mm and less than 5 mm, in particular less than 4 mm.

In a further embodiment according to the second aspect of the invention, the method for producing an undulated hollow fiber membrane is characterized by the engagement depth of the undulating tool's gearwheel teeth amounting to 0.1 to 0.5 mm, in particular 0.1 to 0.2 mm.

In a further embodiment according to the second aspect of the invention, the method for producing an undulated hollow fiber membrane is characterized by the spinning material containing at least one first hydrophobic polymer which is selected from the polyarylether (polysulfone, polyarylketone, polyetherketone), polyamide, polyester, polycarbonate, polyacrylate and methacrylate, polymethacrylimide, polyvinylidenfluoride, polyimide or polyacrylnitrile group or the copolymers comprise corresponding monomer units of the cited polymers or the compounds of the cited polymers, and by the spinning material containing at least one second hydrophilic polymer selected from the polyvinylpyrrolidone or polyethylene glycol group or compounds thereof, and comprises at least one solvent, particularly N-methylpyrrolidone, N,N-dimethyl acetamid, N,N-Diemthylformamide or dimethyl sulfoxide.

In a third aspect, the invention relates to a hollow fiber membrane dialyzer which has a plurality of undulated hollow fiber membranes in accordance with one embodiment pursuant to the first aspect of the invention or is produced according to at least one embodiment pursuant to the second aspect of the invention.

In a fourth aspect of the invention, the invention relates to a method for producing a hollow fiber membrane dialyzer according to the third aspect of the invention, wherein the method comprises the following steps:

Providing a hollow fiber membrane bundle comprising a plurality of hollow fiber membranes in accordance with at least one embodiment pursuant to the first aspect of the invention or obtainable according to at least one embodiment pursuant to the second aspect of the invention, Providing a filter housing, Introducing the hollow fiber membrane bundle into the filter housing and potting the ends of the hollow fiber membranes in the filter housing with a potting compound, Reopening the potted membrane ends so as to enable a flow through the lumen of most of the hollow fibers, and final assembly of the dialyzer, Sterilizing the hollow fiber membrane dialyzer in a heat sterilization process.

In one embodiment according to the fourth aspect, the method for producing a hollow fiber membrane dialyzer is characterized by the heat sterilization comprising a step in which the hollow fiber membrane dialyzer is flushed with water or water vapor heated to 100 to 150° C.

In one embodiment according to the fourth aspect, the method for producing a hollow fiber membrane dialyzer is characterized by the water or water vapor treatment comprising at least one step in which the water or water vapor is conducted into the interior of the hollow fiber membranes and permeates through the membrane wall to the exterior of the fibers under the application of pressure.

In one embodiment according to the fourth aspect, the method for producing a hollow fiber membrane dialyzer is characterized by the hollow fiber membranes being dried at a temperature of from 100° C. to 150° C.

BRIEF DESCRIPTION OF THE FIGURES AND TABLES

Figure 2:
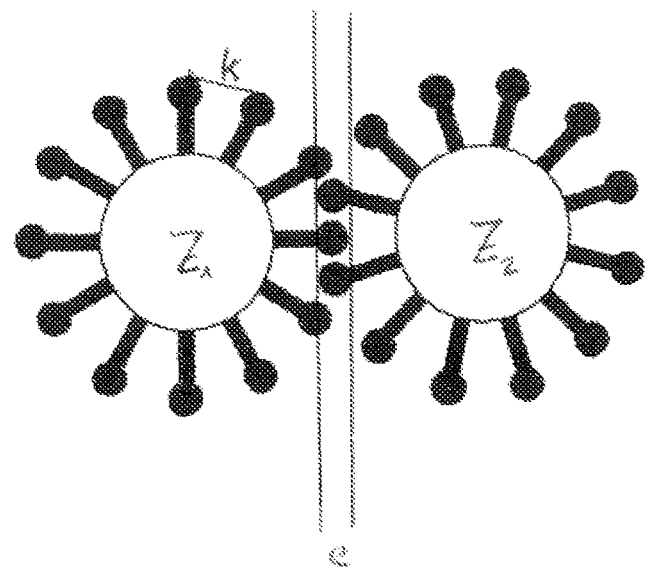

FIG. 1 shows a schematic representation of an undulated hollow fiber membrane according to the invention. Indicated in FIG. 1 are:
λ wavelength
a amplitude
d diameter
l luminal diameter
w wall thickness FIG. 2 schematically depicts an undulating tool having two gearwheels. Indicated in FIG. 2 are:
$Z_1$ first gearwheel
$Z_2$ second gearwheel
k head spacing of two adjacent gearwheel teeth
e engagement depth of the two gearwheels Table 1 shows the sodium clearance of inventive hollow fiber membranes in relation to different wavelengths prior to and after heat sterilization.

DETAILED DESCRIPTION OF THE INVENTION

In a first aspect, the invention relates to an undulated hollow fiber membrane, comprising a first hydrophobic polymer, having a wall thickness of 20 µm or greater and 30 µm or less, wherein the waveform exhibits a wavelength of greater than 1 mm and less than mm, in particular less than 4 mm.

Surprisingly observed in the context of the experimental development of the invention was that a thermostable hollow fiber membrane can be obtained with an undulated hollow fiber membrane having at least one hydrophobic polymer, a wall thickness of 20 µm or greater and 30 µm or less, and with a waveform having a length of more than 1 mm and less than 5 mm. It was in particular proven that there is not such a strongly pronounced drop in clearance from using a heat sterilization process. In particular, the clearance drop in the inventive hollow fiber membrane from a heat sterilization process is so low that an overall rise in the clearance can be observed from the reduced wall thickness compared to a membrane of 35 µm or more.

In the sense of the present application, an "undulated" hollow fiber membrane is to be understood as a hollow fiber membrane exhibiting at least partially concave and convex regions along its longitudinal extension. The concave and convex regions are irregularly or preferentially regularly arranged, i.e. repetitively, along the longitudinal extension of the hollow fiber membrane. The concave and convex regions alternate sequentially and can be spaced apart from each another if need be by a non-concave/non-convex region. The maxima of the concave and convex regions are also referred to as "amplitudes" in the sense of the present application. Different configurations to the inventive hollow fiber membrane are furthermore referred to as undulated in the sense of the present application. In particular, a zigzag configuration or a sawtooth configuration or preferentially a sinusoidal configuration is also referred to as undulated.

In the sense of the present application, the term of "wavelength" means that section in the hollow fiber membrane's longitudinal orientation which corresponds to the distance from one wave amplitude to the second following wave amplitude. This is shown in FIG. 1. In FIG. 1, the wavelength is indicated by λ. Wavelengths can be constant or can vary along the longitudinal orientation of the hollow fiber membrane. Constant wavelengths are preferential.

The term "thermostable" thereby means that the inventive hollow fiber membrane's efficiency data, particularly the clearance, remains largely unchanged when subject to heat. Shown over the course of the heat sterilization was that the amplitude decreases while the wavelength is maintained. If, however, shorter wavelengths greater than 1 mm but less than 5 mm are used in the inventive hollow fiber membranes having wall thicknesses larger than 20 µm and smaller than 30 µm, only a small drop in the clearance occurs after heat sterilization such that the particularly positive properties resulting from the low wall thickness also remain after heat stabilization. The effect is particularly pronounced when the wavelength is shorter than 4 mm.

In particular also understood by the term is that an undulated hollow fiber membrane can be sterilized at heat sterilization conditions above 100° C. without considerable loss to the positive effect of the waveform of the hollow fiber membrane. The stability of the undulated hollow fiber membranes under heat in the present case is, as described, assessed based on the change of the hollow fiber membrane clearance induced by a heat sterilization process. Thus, an inventive undulated hollow fiber membrane can be identified as thermally stable when there is not too great of a decrease in the clearance due to the heat sterilization step. A drop in the sodium clearance of less than 13 ml/min, in particular 12 ml/min or less than 12 ml/min, in particular 10 ml/min or less than 10 ml/min, particularly 8 ml/min or less than 8 ml/min has proven advantageous. Corresponding hollow fiber membranes prove advantageously thermostable.

In further embodiments, the wavelength of the hollow fiber membrane can be at least 1.5 mm or at least 2 mm, or a maximum of 3.5 mm or a maximum of 3 mm. In certain embodiments, the wavelength amounts to 1.5 mm and a maximum of 4 mm, further preferentially at least 2 mm and a maximum of 3.5 mm, further preferentially at least 2 mm and a maximum of 3 mm.

Shorter wavelengths are generally preferential since greater thermostability and less clearance loss is observed with shorter wavelengths. A lower wavelength limit is subject to the buckling stability of the hollow fiber membrane which is in turn subject to the material used, the wall thickness and the amplitude of the waveform. At longer wavelengths of 5 mm or more, undulated hollow fiber membranes having a wall thickness of less than 35 µm are not sufficiently thermostable such that no positive clearance effect can be observed from the reduced wall thickness.

In further embodiments, the undulated hollow fiber membrane wall thickness can amount to at least 22 µm and/or a maximum of 28 µm.

Hollow fiber membranes of reduced wall thickness, in particular less than 30 µm wall thickness, have better moldability than hollow fiber membranes of larger wall thickness. That means that smaller wavelengths can be applied by so-called undulating tools to hollow fiber membranes of reduced wall thicknesses than is the case with hollow fiber membranes having larger wall thickness without the hollow fiber membranes being damaged by kinks or folds.

In the sense of the present application, an "undulating tool" refers to an apparatus with which an "undulation," i.e. a waveform, can be disposed on a linear hollow fiber membrane. The "waveform" of a hollow fiber membrane is defined by its wave-shaped configuration as described in paragraph [038]. Generally speaking, the waveform is mechanically produced on the hollow fiber membrane during the production of the hollow fiber membranes. FIG. 2 schematically depicts a typical undulating tool.

In one preferential embodiment according to the first aspect of the invention, the undulated hollow fiber membrane is characterized by the waveform of the hollow fiber membrane having an amplitude ranging from 0.005 to 0.15 mm. Amplitudes of 0.01 mm to 0.12 mm are preferential.

In general, each outward curve of the undulated hollow fiber membrane can be considered inventive, irrespective of the specific waveform defining the inventive hollow fiber membrane. In this sense, the term amplitude can also describe zigzagging or sawtooth-like waveforms. One inventive form of the outward curve is periodic. With the example of a periodic wave, the amplitude in the sense of the present application is understood as half the horizontal distance between a wave trough and a wave crest. This is shown in FIG. 1. The amplitude is indicated by "a" in FIG. 1. "Wave trough" and "wave crest" is thereby to be understood as indicating two adjacent curves of the hollow fiber membrane. The periodic wave of the FIG. 1 is sinusoidal in this example.

The amplitude of the inventive undulated hollow fiber membrane can amount to at least 0.01 mm or at least 0.02 mm, or a maximum of 0.12 or a maximum of 0.1 mm. In one embodiment, the amplitude of the undulated hollow fiber membranes amounts to at least 0.02 mm to a maximum of 0.12 mm, or preferentially at least 0.04 mm to 0.12 mm.

The disposing of waveforms onto hollow fiber membranes of larger amplitude at the given wall thickness and wavelength is generally limited to the buckling stability of the hollow fiber membrane. Large amplitudes are however desirable in terms of the separation efficiency because they effect a better hollow fiber membrane spacing in the hollow fiber membrane bundle or in the hollow fiber membrane dialyzer respectively. The hollow fiber membrane spacing in the hollow fiber membrane dialyzer yields better dialysate inflow vis-à-vis the hollow fiber membrane and thus also a better clearance. On the other hand, the trend to the hollow fiber membrane spacing and thus also the dialysate inflow in the hollow fiber membrane dialyzer are in principle reduced with undulated hollow fiber membranes of low amplitude. However, surprisingly shown was a low amplitude already enabling very good clearance values and a low drop in clearance for hollow fiber membranes of low wall thickness coupled with short wavelengths within each respective inventive range. Comparatively low amplitudes can also ensure a particularly gentle extracorporeal blood treatment.

In one embodiment according to the first aspect of the invention, the undulated hollow fiber membrane is characterized by the hollow fiber membrane exhibiting a luminal diameter of 160 to 230 µm. The term "luminal diameter" indicates the inner width inside the hollow fiber membrane measured at a cross section perpendicular to the longitudinal orientation of the hollow fiber membrane. This is shown in FIG. 1.

The inventive hollow fiber membrane exhibits a luminal diameter of at least 160 µm or at least 170 µm or at least 180 µm, or a maximum of 230 µm or a maximum of 210 µm or a maximum of 200 µm. In one embodiment, the luminal diameter amounts to at least 170 µm to a maximum of 230 µm, preferentially 180 µm to a maximum of 230 µm.

The luminal diameter of a hollow fiber membrane is associated with the stability of the hollow fiber membrane. In particular, hollow fiber membrane stability is negatively affected with hollow fiber membranes of reduced wall thickness below 31 µm. A hollow fiber membrane of large luminal diameter tends to be deformed or damaged under mechanical influences. This can in particular be the case when a hollow fiber membrane is processed by an undulating tool in order to produce a waveform. In contrast, smaller luminal diameters increase the stability of hollow fiber membranes of low wall thicknesses vis-à-vis mechanical effects. A lower luminal diameter limit is a condition of using the hollow fiber membrane for treating blood. Luminal diameters below 160 µm do not prove practicable from a therapeutic perspective. Luminal diameters of at least 180 µm are preferential because particularly gentle blood treatment is possible with such implementations.

In one embodiment according to the first aspect of the invention, the undulated hollow fiber membrane is characterized by the waveform being substantially sinusoidal, in particular sinusoidal.

Identifying an undulated hollow fiber membrane as a "sinusoidal" waveform is to be understood in the context of the present application as the concave and convex regions of the inventive hollow fiber membrane being uniform and regular along the longitudinal extension; i.e. having a substantially constant wavelength and constant amplitude and approximating the form of a sine function in the mathematical sense.

Such sinusoidal waveforms of hollow fiber membranes are advantageous in the production. Furthermore, the spacing of the hollow fiber membranes in a hollow fiber membrane dialyzer or a hollow fiber membrane bundle is advantageous.

According to a further development of the invention, the inventive hollow fiber membrane is characterized by at least one first hydrophobic polymer being selected from the polyarylether (polysulfone, polyarylketone, polyetherketone), polyamide, polyester, polycarbonate, polyacrylate and methacrylate, polymethacrylimide, polyvinylidenfluoride, polyimide or polyacrylnitrile group or the copolymers comprising corresponding monomer units of the cited polymers or the compounds of the cited polymers.

A further embodiment is characterized by the hollow fiber membrane comprising at least one second hydrophilic polymer and by the at least one second polymer being selected from the polyvinylpyrrolidone or polyethylene glycol group or compounds thereof.

As defined by the present application, "hydrophobic polymers" refer to polymers which are not soluble in water. "Hydrophilic polymers" refer to polymers which are soluble in water or which form hydrogels.

According to the invention, the at least one hydrophobic polymer forms the major portion of the polymer material from which the inventive hollow fiber membranes are produced. The pore structure of the inventive hollow fiber membrane is formed by the at least one first hydrophobic polymer material and yields the exclusion/separating behavior of the hollow fiber membranes. A low proportion of the at least one second hydrophilic polymer is present in the membrane material of the hollow fiber membranes. The at least one second hydrophilic polymer is deposited on the hollow fiber membrane close to the surface and effects the wettability of the hollow fiber membrane by aqueous treatment fluids such as e.g. blood or dialysate. Furthermore, in addition to a solvent, the hydrophilic polymers are responsible for the pore formation during the production of hollow fiber membranes in a spinning and phase inversion process.

The at least one first hydrophobic polymer is preferentially a polysulfone and is characterized by the hollow fiber membranes produced therefrom being particularly well-suited to heat sterilization.

A polymer referred to as "polysulfone" in the context of the present application is to be understood as a polymer having at least one sulfone group in the polymer main or side chain. Typical examples of polysulfones are: polysulfone (PSU), polyether sulfone (PES), polyphenylsulfone and copolymers containing at least one sulfone group. Further examples of polysulfone polymers are known in the prior art and are suited to producing blood treatment membranes in the sense of the invention.

In further embodiments, the undulated hollow fiber membrane is characterized by the at least second hydrophilic polymer being selected from the polyvinylpyrrolidone or polyethylene glycol group or compounds thereof. The polyvinylpyrrolidone group is particularly preferential as polyvinylpyrrolidones can be heat-sterilized and are preferential with respect to producing the hollow fiber membranes in a spinning and phase inversion process in conjunction with at least one hydrophobic polymer, particularly polysulfones. Polyvinylpyrrolidones are additionally especially hemo-compatible; i.e. with no or only minor adverse effects to the blood stemming from the polymer. This applies in particular in conjunction with a polysulfone as the hydrophobic polymer.

Identifying a polymer as a "polyvinylpyrrolidone" is to be understood in the sense of the present application as a polymer which is produced using the vinylpyrrolidone monomer or derivatives thereof.

In further embodiments, the undulated hollow fiber membrane is characterized by the porosity of the hollow fiber membrane being greater than 65%, in particular greater than 70%, further particularly greater than 72%. Apart from reducing the wall thickness, a suitable measure of improving the diffusion properties of a hollow fiber membrane with lasting effect is increasing porosity. Disadvantageous with increasing porosity, however, as is with reducing wall thickness, is that the mechanical and thermal stability is lowered. Thus, increasing porosity does not inevitably lead to improving the clearance, particularly when a heat sterilization step has been performed. However, particularly high clearance values are achieved, even after heat sterilization, when hollow fiber membranes of low wall thickness, in particular a wall thickness of 30 µm or less, and high porosity of greater than 65% is provided with the inventive wave-like undulation. Particularly preferential hollow fiber membranes of high porosity are thereby substantially free, in particular completely free, of so-called dendritic cavities or "macrovoids." Substantially free of macrovoids thereby means that less than 5% of the wall volume of the porous hollow fiber membrane is occupied by such macrovoids.

A further embodiment provides for the porosity of the hollow fiber membrane to be greater than 65%, in particular greater than 70%, and further particularly greater than 72% and less than 78%, in particular less than 76%. It was shown that especially the porosity of hollow fiber membranes of low wall thickness between 20 and 30 µm should be regulated so as to achieve the optimal desired efficiency parameters.

A second aspect of the invention relates to a method for producing an inventive hollow fiber membrane, wherein the method comprises the following steps:

Producing a hollow fiber membrane having a wall thickness of 20 µm or greater and 30 µm or less from a spinning material in a spinning and phase inversion process, Providing at least one undulating tool, and orientating the undulating tool if need be, in order to produce an undulated structure of predetermined wavelength and amplitude, Processing the hollow fiber membrane with the undulating tool so as to result in an undulation wavelength of more than 1 mm and less than 5 mm, in particular less than 4 mm.

The terms "spinning process" and "phase inversion process" are sufficiently known in the prior art in connection with the production of hollow fiber membranes. They are for example described in the DE 102016224627.5 application. The disclosure of DE102016224627.5 is thus part of the present application.

According to one embodiment of the second aspect of the invention, the undulating tool is a gearing as the example of FIG. 2 shows. FIG. 2 shows two gearwheels $Z_1$ and $Z_2$, which are constructed such that the gearwheels engage and can be moved in opposite rotation to each other. In particular, an undulating tool according to this embodiment can be constructed such that the engagement depth of the gearwheels can be adjusted by moving the gearwheels toward/ away from each other. In order to dispose a waveform on a hollow fiber membrane, a hollow fiber membrane is passed between the engaged gearwheels. The engaged gearwheels effect a tensile stress on the hollow fiber membrane such that the hollow fiber membrane is deformed differently in recurrent sections subject to the action of the engaging teeth of the gearwheels. As a result, an undulated hollow fiber membrane forms from the repetitively differing deformation. The form of the teeth and the engagement depth are thereby adapted such that there is ideally no pinching of the hollow fiber membranes to cause a deformed hollow fiber membrane cross section.

The undulating tool's gearwheel teeth have a head spacing of less than 5 mm.

In the sense of the present application, the term "head spacing" indicates the distance between two adjacent gearwheel teeth. All the teeth of a gearwheel are thereby equally spaced from one another. The head spacing of the teeth effects the wavelength of the hollow fiber membrane. The head spacing of the teeth is identified in FIG. 2 as "k."

In particular, the head spacing can be greater than 1 mm, or at least 15 mm, or at least 2 mm, or less than 5 mm, or a maximum of 4 mm or a maximum of 3.5 mm or a maximum of 3 mm. In one embodiment, the head spacing amounts to more than 1 mm and less than 5 mm, preferentially at least 1.5 mm and a maximum of 4 mm, further pre-ferentially at least 2 mm and a maximum of 3.5 mm, further preferentially at least 2 mm and a maximum of 3 mm.

In one embodiment, the engagement depth of the undulating tool's gearwheels amounts to 0.1 to 0.5 mm, in particular 0.1 to 0.2 mm. The engagement depth of the gearwheels effects the height of the amplitudes of the undulated hollow fiber membrane. A lesser engagement depth produces a low amplitude, whereby a greater engagement depth produces a high amplitude. The engagement depth of the gearwheels is governed by the height of the amplitude which the inventive hollow fiber membrane is to exhibit. According to the invention, the resulting amplitude of the hollow fiber membrane is smaller than the engagement depth of the gearwheels. Introducing the waveform by means of the gearwheels is particularly economical and leads to particularly well-defined uniform waveforms, in particular to repetitive, further particularly sinusoidal waveforms compared to other known prior art methods. This results in high clearance values.

According to a further development of the inventive method for producing an undulated hollow fiber membrane, the spinning material contains at least one first hydrophobic polymer, in particular selected from the polyarylether (polysulfone, polyarylketone, polyetherketone), polyimide, polyester, polycarbonate, polyacrylate and methacrylate, polymethacrylimide, polyvinylidenfluoride, polyimide or polyacrylnitrile group, the copolymers comprising corresponding monomer units of the cited polymers or the compounds of the cited polymers, and the spinning material further contains at least one second at least hydrophilic polymer, in particular selected from the polyvinylpyrrolidone or polyethylene glycol group or compounds thereof as well as at least one solvent, in particular N-methylpyrrolidone, N,N-dimethyl acetamid, N,N-Diemthylformamide or dimethyl sulfoxide.

Hollow fiber membranes from the cited materials prove to be sufficiently stable enough to produce thermostable, deformation-resistant inventive undulated hollow fiber membranes of reduced wall thickness of 30 µm or less able to be subjected to heat sterilization. The term "deformation-resistant" hereby refers to the stability requirements a hollow fiber membrane is to exhibit in order to remain undamaged during the processing of the hollow fiber membrane while the hollow fiber membrane and waveform is being produced.

In a third aspect, the invention relates to a hollow fiber membrane dialyzer comprising a plurality of inventive hollow fiber membranes.

The inventive hollow fiber membrane dialyzer is characterized by its ability to be heat sterilized without any excessive adverse effects to the advantageous separative properties of the inventive hollow fiber membrane of 30 µm or less wall thickness caused by the heat sterilization. A hollow fiber membrane dialyzer can thus be provided which exhibits improved properties in terms of clearance, in particular improved clearance properties, compared to hollow fiber membrane dialyzers having hollow fiber membranes with a wall thickness greater than 30 µm and the same effective membrane surface. Furthermore advantageous is the reduced wall thickness of the inventive hollow fiber membranes resulting in less membrane material being needed when constructing an inventive hollow fiber membrane dialyzer having the same number of hollow fiber membranes and the same effective membrane surface compared to hollow fiber membranes of greater wall thickness. The inventive hollow fiber membrane dialyzer can thus be constructed more economically and sparing of raw material. Additionally, the filter housing can be of smaller and more compact design.

In the sense of the present application, the term "effective membrane surface" refers to the surface of the hollow fiber membranes in a hollow fiber membrane dialyzer in contact with the fluid to be filtered, in particular blood.

The membrane surface can be calculated from the hollow fiber geometrical data.

In a fourth aspect, the invention relates to a method for producing a hollow fiber membrane dialyzer in accordance with the third aspect of the invention, characterized by the method comprising the steps:

Providing a hollow fiber membrane bundle comprising a plurality of hollow fiber membranes pursuant to at least one embodiment in accordance with the first aspect of the invention or produced pursuant to at least one embodiment in accordance with the second aspect of the invention, Providing a filter housing, Introducing the hollow fiber membrane bundle into the filter housing and potting the ends of the hollow fiber membranes in the filter housing with a potting compound, Reopening the potted membrane ends so that a flow is enabled through the lumen of most of the hollow fibers, and final assembly of the dialyzer, Sterilizing the hollow fiber membrane dialyzer in a heat sterilization process.

The inventive method for producing a hollow fiber membrane dialyzer comprises the steps of constructing the filter and heat-sterilizing the hollow fiber membrane dialyzer. In one embodiment, the hollow fiber membrane production steps pursuant to one embodiment in accordance with the second aspect of the invention precedes said method. According thereto, inventive hollow fiber membranes pursuant to the first aspect of the invention or those hollow fiber membranes obtained pursuant to an embodiment in accordance with the second aspect of the invention are combined into hollow fiber membrane bundles. The method steps of bundling hollow fiber membranes, introducing the hollow fiber membrane bundle into a housing of a hollow fiber membrane dialyzer, the potting of the ends of the hollow fiber membranes in the housing and the reopening of the potted membrane ends are known methods already being used on a mass production scale. The term "so that a flow is enabled through the lumen of most of the hollow fibers" is to understand as more than 98% of all the hollow fibers of the hollow fiber bundle being clear to the test fluids of an efficiency test or, respectively, to the blood when employed in dialysis after the reopening step.

The heat sterilization process can be designed such that the inventive hollow fiber membrane dialyzer can be flushed with water or water vapor heated to 100 to 150° C. The flushing process can in particular be conducted such that the inventive hollow fiber membrane dialyzer and inventive hollow fiber membranes are evenly heated.

In a further preferential embodiment, the method for producing a hollow fiber membrane dialyzer is characterized by the water or water vapor treatment comprising at least one step in which the water or water vapor is conducted into the interior of the hollow fiber membrane and permeates through the membrane wall to the exterior of the fibers under the application of pressure. This method is described in DE 102016224627.5 and is hereby part of the present application. This method enables par-ticularly reliable flushing and heat sterilization. Moreover, the extent of clustered hollow fibers on the dialysate side is reduced, which improves the hollow fiber membrane-dialysate exchange. This effect is particularly pronounced when inventive hollow fibers of low wall thickness of 30 μm and less are used in combination with an undulation wavelength of more than 1 mm and less than 5 mm, in particular less than 4 mm. It was surprisingly shown that the effect remains fully the same even at very low amplitudes.

A further embodiment provides for the method for producing an inventive hollow fiber membrane dialyzer to be characterized by the hollow fibers being dried at 100 to 150° C. Such high drying temperatures lead to a very effective time-optimized drying process without too great of a decline in the inventive hollow fiber membrane dialyzer's efficiency data. Thus, an effectively manufactured filter having high efficiency data can be provided.

EXAMPLES AND METHODS

The following will make use of examples in describing the invention in greater detail without, however, being limited thereto.

Measurement Method 1: Sodium Ion Clearance Determination

The clearance is determined on a hollow fiber membrane dialyzer constructed as per Ex. 5 based on the DIN EN ISO 8637:2014. Differing from No. 6.1.2 of the standard, an aqueous solution of sodium chloride at a concentration of 5 g/l is used as the test solution for the blood region. Distilled water is used for the dialysate region. The sodium ion concentrations are determined by measuring conductivity. On the blood side of the hollow fiber membrane dialyzer, the test solution flow rate is set at 300 ml/min. On the dialysate side, the distilled water flow rate is set at 500 ml/min. The blood side and dialysate side flows run in counterflow to each other. The temperatures of the fluids are set at 37° C.

Measurement Method 2: Porosity Determination

A hollow fiber membrane bundle consisting of identical hollow fiber membranes which was previously dried in a drying chamber for 2 hours at 105° C. is weighed. The average length of the fibers, the average inner diameter and the average outer diameter, and the number of fibers is determined. The average dimensions are determined for at least 10 different fibers of the hollow fiber membrane bundle. A constant temperature of 20° C. is maintained when determining the dimensions. From the dimensions, a volume taken through the membrane walls of the hollow fiber membranes of the hollow fiber membrane bundle is determined under assumption of the geometry of the hollow fiber membranes corresponding to a hollow cylinder. The average density of the membrane structure within the hollow fiber membranes can be calculated from the determined volume and measured weight. The percentile porosity results from the ratio of determined to theoretical hollow fiber membrane density at full polymer compactness according to the following formula:

$$\text{Porosity} = \frac{(\text{compacted polymer density} - \text{measured fiber density})}{\text{compacted polymer density}} * 100$$

Example 1: Producing an Inventive Undulated Hollow Fiber Membrane

A spinning solution consisting of 16 parts by weight of polysulfone (P3500 from the Solvay company), 4.4 parts by weight of polyvinylpyrrolidone (K82-86 from the Ashland company) and 79.6 parts by weight of DMAC is heated to 60° C. under agitation, thereafter degassed and processed into a homogeneous spinning material. The spinning material is extruded into a strand through a circular annular nozzle along with a centrally controlled precipitant consisting of 35% dimethylacetamide (DMAc) and 65% water. The annular gap has a gap width of 50 μm and an inner diameter of 200 μm. The precipitant is fed into the interior of the hollow strand. The temperature of the annular nozzle amounts to 70° C. The extruded strand is guided through a precipitant chamber, the atmosphere of which has a relative humidity of 100%. The height of the precipitation gap amounts to 200 mm, a precipitation gap dwell time of 0.4 seconds is set. The strand is introduced into a precipitation bath consisting of water kept at 80° C. and precipitated into a hollow fiber membrane. The hollow fiber membrane is subsequently guided through rinsing baths kept at a temperature of 75° C. to 90° C. The hollow fiber membrane thereafter undergoes a drying process between 100° C. and 150° C. A hollow fiber membrane having a wall thickness of 25 μm and a luminal diameter of 185 μm results. The porosity of the membrane amounts to 73%.

The hollow fiber membrane thereby obtained is then led through an undulating tool having two intermeshing gearwheels. The heads of the gearwheel teeth are at a spacing of 2 mm. The engagement depth of the gearwheels amounts to 0.150 mm. The undulating tool is kept at 125° C. The undulated hollow fiber membrane obtained exhibits a wavelength of 2 mm and an amplitude of 0.1 mm.

Example 2: Producing an Inventive Undulated Hollow Fiber Membrane

A hollow fiber membrane is produced via the spinning method according to Ex. 1. The hollow fiber membrane obtained is led through an undulating tool kept at 125° C., wherein the heads of the gearwheel teeth are at a spacing of 3 mm. The engagement depth of the gearwheels amounts to 0.150 mm. The undulated hollow fiber membrane obtained exhibits a wavelength of 3 mm and an amplitude of 0.1 mm.

Example 3: Producing an Inventive Undulated Hollow Fiber Membrane

A hollow fiber membrane is produced via the spinning method according to Ex. 1. The hollow fiber membrane obtained is led through an undulating tool kept at 125° C., wherein the heads of the gearwheel teeth are at a spacing of 4 mm. The engagement depth of the gearwheels amounts to 0.150 mm. The undulated hollow fiber membrane obtained exhibits a wavelength of 4 mm and an amplitude of 0.1 mm.

Comparative Example 1: Producing an Undulated Hollow Fiber Membrane

A hollow fiber membrane is produced via the spinning method according to Ex. 1. The hollow fiber membrane obtained is led through an undulating tool kept at 125° C., wherein the heads of the gearwheel teeth are at a spacing of 5 mm. The engagement depth of the gearwheels amounts to 0.160 mm. The undulated hollow fiber membrane obtained exhibits a wavelength of 5 mm and an amplitude of 0.1 mm.

Comparative Example 2: Producing an Undulated Hollow Fiber Membrane

A hollow fiber membrane is produced via the spinning method according to Ex. 1. The hollow fiber membrane obtained is led through an undulating tool kept at 125° C., wherein the heads of the gearwheel teeth are at a spacing of 8.8 mm. The engagement depth of the gearwheels amounts to 0.2 mm. The undulated hollow fiber membrane obtained exhibits a wavelength of 8.8 mm and an amplitude of 0.11 mm.

Comparative Example 3: Producing an Undulated Hollow Fiber Membrane

A hollow fiber membrane is produced via the spinning method according to Ex. 1. The hollow fiber membrane obtained is led through an undulating tool kept at 125° C., wherein the heads of the gearwheel teeth are at a spacing of 1 mm. The engagement depth of the gearwheels amounts to 0.15 mm. The hollow fiber membrane obtained exhibits foldings in the region of the undulations and is of only limited passability to fluids.

Comparative Example 4: Producing an Undulated Hollow Fiber Membrane

A hollow fiber membrane is produced via the spinning method according to Ex. 1, wherein a deviating wall thickness to the hollow fiber membrane of 35 μm is selected at the same luminal diameter of 185 μm. The hollow fiber membrane obtained is led through an undulating tool kept at 125° C., wherein the heads of the gearwheel teeth are at a spacing of 7.3 mm. The engagement depth of the gearwheels amounts to 0.3 mm. The undulated hollow fiber membrane obtained exhibits a wavelength of 7.2 mm and an amplitude of 0.2 mm. The porosity of the membrane amounts to 79.9%. The porosity is clearly higher due to the greater wall thickness.

Example 4: Producing an Inventive Hollow Fiber Membrane Dialyzer

The undulated hollow fiber membranes obtained pursuant to examples 1 to 3 and comparative examples 1 to 3 are looped onto a reel and consolidated into a tow. Hollow fiber membrane bundles are produced from the spooled tow. In the process, 9984 hollow fiber membranes of the hollow fiber membranes produced are consolidated into a bundle and introduced into a housing of a hollow fiber membrane dialyzer having an inner diameter of 28.8 mm. The length of the hollow fiber membranes amounts to 279 mm. The ends of the hollow fiber membranes are potted in the housing of the hollow fiber membrane dialyzer so that a first chamber (blood side) is formed in the constructed hollow fiber membrane dialyzer which encompasses the interior of the hollow fiber membranes and a second chamber (dialysate side) is further formed which encompasses the space between the hollow fiber membranes. Polyurethane from the Elastogran company (polyol C6947 and isocyanate 136-20) is used as the potting material. The potting height at each bundle end amounts to 22 mm. The effective membrane surface of the hollow fiber membrane dialyzer amounts to 1.3 m². Table 1 depicts the results of the clearance determination for different hollow fiber membrane dialyzers pursuant to Ex. 4 with respectively different undulated hollow fiber membranes pursuant to examples 1 to 3 and comparative examples 1 and 2. Measurement values cannot be determined for comparative example 3. The following data differs in the case of comparative example 4: 10752 hollow fibers are used for the hollow fiber membrane bundle. That results in an effective membrane surface of 1.4 m². This bundle is set into a housing having an inner diameter of 33.8 mm. The measured values of comparative example 2 are indicated in Table 2.

Example 5: Producing a Sterile Hollow Fiber Membrane Dialyzer

The undulated hollow fiber membranes obtained pursuant to examples 1 to 3 and comparative examples 1 to 4 are used to obtain an assembled hollow fiber membrane dialyzer as per Ex. 4. The thus obtained hollow fiber membrane dialyzer is subjected to steam sterilization. The steam sterilization method is described in detail in the DE 102016224627.5 application. The hollow fiber membrane dialyzer is thereby connected to a sterilizing apparatus and the procedural steps as per DE 102016224627.5 performed. The hollow fiber membrane dialyzer is subsequently uncoupled from the sterilizing apparatus and tightly sealed. The sodium ion clearance is thereafter determined on the hollow fiber membrane dialyzer as obtained and sterilized. Table 1 depicts the results of the clearance determination for different hollow fiber membrane dialyzers according to Ex. 5 with respective differently undulated hollow fiber membranes pursuant to examples 1 to 3 and comparative examples 1 and 2. Measurement values cannot be determined for comparative example 3. Comparative example 4 is depicted in Table 2.

The tables show the sodium clearance values obtained for the hollow fiber membrane dialyzer obtained in non-sterile condition pursuant to Ex. 4 and in sterile condition pursuant to Ex. 5 for hollow fiber membranes having wavelengths between 2 and 8.8 mm.

TABLE 1

| | Wavelength (mm) | Clearance (ml/min.) non-sterile | Clearance (ml/min.) sterile | Difference (ml/min.) | Wall thickness (μm) |
|---|---|---|---|---|---|
| Comp. Ex. 3 | 1 | — | — | — | 25 |

TABLE 1-continued

|      | Wavelength (mm) | Clearance (ml/min.) non-sterile | Clearance (ml/min.) sterile | Difference (ml/min.) | Wall thickness (μm) |
|---|---|---|---|---|---|
| Ex. 1 | 2 | 285 | 278 | 7 | 25 |
| Ex. 2 | 3 | 285 | 279 | 6 | 25 |
| Ex. 3 | 4 | 280 | 268 | 12 | 25 |
| Comp. Ex. 1 | 5 | 276 | 262 | 14 | 25 |
| Comp. Ex. 2 | 8.8 | 269 | 255 | 14 | 25 |

TABLE 2

|      | Wavelength (mm) | Clearance (ml/min.) non-sterile | Clearance (ml/min.) sterile | Difference (ml/min.) | Wall thickness (μm) |
|---|---|---|---|---|---|
| Comp. Ex. 4 | 7.2 | 278 | 265 | 13 | 35 |

It is shown that when using hollow fibers having a wall thickness of 25 μm, a particularly high clearance of 280 ml/min. or more is then obtained when an undulation wavelength below 5 mm is selected. It is further shown that clearance values following the steam sterilization drop less than 13 ml/min. when a wavelength below 5 mm is selected. It is further shown in a particularly preferential embodiment that clearance values following the steam sterilization drop less than 10 ml/min. when a wavelength below 4 mm is selected. If too low of a wavelength is selected, which occurs at a length of 1 mm, sufficient flow through the filter can no longer be ensured due to the membranes previously suffering folding damage.

Due to the greater dimensions of the fibers, a modified number of fibers and a different housing dimension was selected for comparative example 4. It is shown that despite a larger effective membrane surface, comparative example 4 exhibits clearly lower clearance both before as well as after heat sterilization.

The invention claimed is:

1. An undulated hollow fiber membrane, comprising at least one first hydrophobic polymer and at least one second hydrophilic polymer, having a wall thickness of 20 μm or greater and 30 μm or less, wherein the at least one first hydrophobic polymer is a polyarylether, polyamide, polyester, polycarbonate, polyacrylate and methacrylate, polymethacrylimide, polyvinylidenfluoride, polyimide, polyacrylnitrile group, or any copolymer thereof, and the at least one second hydrophilic polymer is a polyvinylpyrrolidone or polyethylene glycol group, and a waveform of the hollow fiber membrane exhibits a wavelength in a range of from greater than 1 mm and less than 4 mm and wherein a porosity of the hollow fiber membrane is 65% to less than 78%, and a drop in sodium clearance of the hollow fiber membrane is less than 13 ml/min after a heat sterilization process of above 100° C.

2. The hollow fiber membrane according to claim 1, wherein the waveform has an amplitude in a range of from 0.005 to 0.15 mm.

3. The hollow fiber membrane according to claim 1, wherein the hollow fiber membrane has a luminal diameter of from 160 to 230 μm.

4. The hollow fiber membrane according to claim 1, wherein the waveform is substantially sinusoidal.

5. The hollow fiber membrane according to claim 2, wherein the amplitude is from 0.01 to 0.12 mm.

6. A method for producing an undulated hollow fiber membrane containing at least one first hydrophobic polymer, comprising the steps:
producing a hollow fiber membrane having a wall thickness of 20 μm or greater and 30 μm or less and having a porosity of 65% to less than 78% from a spinning material in a spinning and phase inversion process;
producing a waveform of predetermined wavelength and amplitude with at least one undulating tool; and
processing the hollow fiber membrane with the at least one undulating tool so as to yield an undulation wavelength of more than 1 mm and less than 4 mm, wherein a drop in sodium clearance of the hollow fiber membrane is less than 13 ml/min after a heat sterilization process of above 100° C.

7. The method for producing a hollow fiber membrane according to claim 6, wherein the at least one undulating tool comprises two intermeshing gears between which the hollow fiber membrane is passed.

8. The method for producing a hollow fiber membrane according to claim 6, wherein an engagement depth of teeth of the at least one undulating tool amounts to 0.1 to 0.5 mm.

9. The method for producing a hollow fiber membrane according to claim 6, wherein the spinning material contains at least one first hydrophobic polymer that is a polyarylether, polyamide, polyester, polycarbonate, polyacrylate and methacrylate, polymethacrylimide, polyvinylidenfluoride, polyimide or polyacrylnitrile group or any copolymer thereof, and the spinning material contains at least one second hydrophilic polymer that is a polyvinylpyrrolidone or polyethylene glycol group, and at least one solvent.

10. The method for producing a hollow fiber membrane according to claim 9, wherein said at least one solvent is methylpyrrolidone, N,N-dimethyl acetamide, N,N-Diemthylformamide or dimethyl sulfoxide.

11. A hollow fiber membrane dialyzer comprising a plurality of the hollow fiber membrane in accordance with claim 1.

12. A method for producing a hollow fiber membrane dialyzer comprising the steps:
providing a hollow fiber membrane bundle comprising a plurality of the hollow fiber membrane in accordance with claim 1;
providing a filter housing;
introducing the hollow fiber membrane bundle into the filter housing and potting ends of the hollow fiber membranes in the filter housing with a potting compound to form a potted membrane;
reopening the ends of the potted membrane so as to enable a flow through a lumen of most of the hollow fiber membranes, and final assembly of the hollow fiber membrane dialyzer; and
sterilizing the hollow fiber membrane dialyzer in the heat sterilization process.

13. The method for producing a hollow fiber membrane dialyzer according to claim 12, wherein the heat sterilization process comprises a step in which the hollow fiber membrane dialyzer is flushed with water or water vapor heated to 100 to 150° C.

14. The method for producing a hollow fiber membrane dialyzer according to claim 13, wherein the water or water vapor is conducted into an interior of the hollow fiber membranes and permeates through a membrane wall to an exterior of the hollow fiber membranes under application of pressure.

15. The method for producing a hollow fiber membrane dialyzer according to claim 12, wherein the hollow fiber membranes are dried at a temperature of from 100° C. to 150° C.

* * * * *